United States Patent [19]
Chandran et al.

[11] Patent Number: 5,478,553
[45] Date of Patent: Dec. 26, 1995

[54] HAIR FIXATIVE COMPOSITIONS CONTAINING POLYMERIC N-VINYL FORMAMIDE

[75] Inventors: Rama S. Chandran, S. Bound Brook; Jean-Pierre Leblanc, Somerville; John C. Leighton, Flanders; Gary T. Martino, Plainsboro, all of N.J.

[73] Assignee: National Starch and Chemical Investment Holding Corporation, Wilmington, Del.

[21] Appl. No.: 286,850

[22] Filed: Aug. 5, 1994

[51] Int. Cl.$^6$ .............. A61K 7/11; C08F 220/54
[52] U.S. Cl. .............. 424/70.17; 424/70.16; 526/307.1; 526/307.4
[58] Field of Search .............. 424/70, 70.11, 424/70.17, 70.16; 526/307.1, 310, 312

[56] References Cited

U.S. PATENT DOCUMENTS

| | | | |
|---|---|---|---|
| Re. 34,713 | 9/1994 | Itagaki et al. | 526/307 |
| 2,628,224 | 2/1953 | Cairns et al. | 526/307 |
| 3,212,972 | 10/1965 | Bailey, Jr. et al. | 424/70 |
| 4,421,602 | 12/1985 | Brunnmueller et al. | 162/168.2 |
| 4,578,515 | 3/1986 | Dawson et al. | 564/215 |
| 4,623,699 | 11/1986 | Brunnmueller et al. | 525/355 |
| 4,906,777 | 3/1990 | Pinschmidt, Jr. et al. | 564/215 |
| 4,942,259 | 7/1990 | Parris et al. | 564/187 |
| 5,021,238 | 6/1991 | Martino et al. | 424/47 |
| 5,037,927 | 8/1991 | Itagaki et al. | 526/307.7 |
| 5,064,909 | 11/1991 | Itagaki et al. | 525/340 |
| 5,270,379 | 12/1993 | McAndrew et al. | 524/555 |

FOREIGN PATENT DOCUMENTS 2040601  4/1991  Canada .

*Primary Examiner*—Peter F. Kulkosky
*Attorney, Agent, or Firm*—William K. Wissing

[57] ABSTRACT

The present invention relates to hair fixative compositions which utilize as the hair fixative resin a polymer which is prepared from N-vinyl formamide (NVF). The polymer may be a homopolymer of NVF or an interpolymer of NVF and at least one vinyl monomer(s). The polymer is present in amounts effective to provide the inventive hair fixative compositions with hair fixative properties. In preferred embodiments, the hair fixative composition is a stable, aqueous gel which forms a clear, non-tacky film upon drying. In certain embodiments, the gel has a rheology effective to allow the gel to be applied to the hair via a spray pump.

19 Claims, No Drawings

HAIR FIXATIVE COMPOSITIONS CONTAINING POLYMERIC N-VINYL FORMAMIDE

FIELD OF THE INVENTION

This invention relates to hair fixative compositions which utilize as a hair fixative resin polymers prepared from N-vinyl formamide.

BACKGROUND OF THE INVENTION

In their most basic form, hair fixative compositions contain a film-forming resin, typically a polymer, which acts as the hair fixative in the composition. The resin can be applied to the hair in the form of a spray, either via a spray pump or an aerosol spray, or in the form of a gel.

In aerosol hair spray systems, the resin usually is dissolved in an organic solvent, such as ethanol or isopropyl alcohol, and delivered via a propellant, which is usually a volatile hydrocarbon. These systems are becoming less desirable due to the consumers' perception that alcohol in hair sprays can dry and damage hair, and due to environmental regulations limiting the emission of volatile organic compounds (VOC) into the atmosphere. As used herein, a volatile organic compound is an organic compound containing at least one, but not more than 10, carbon atoms, except for those organic compounds having a vapor pressure of less than 0.1 mm Hg at 20° C. There is an on-going effort by the hair care industry to replace the VOC with water. However, the inclusion of significant amounts of water in hair fixative compositions has created problems relating to solubility and dispersability of the hair fixative resin in the compositions, to application of the hair fixatives to the hair and to performance of the hair fixative once applied to the hair.

There is a need in the industry for low VOC, aqueous-based, hair fixative compositions and hair fixative polymers which are dispersable or soluble in water, which can be applied readily to the hair, and which provide acceptable hair fixative properties, such as strength, i.e., holding power or stiffness, humidity resistance, film clarity, aesthetics and removability from hair using conventional shampoo and/or water.

One such approach to lower VOC hair fixatives is disclosed in U.S. Pat. No. 5,021,238, in the name of Martino et al. Two-phase, aqueous-based, hair-fixing aerosol systems which utilize dimethyl ether as a propellant are disclosed. The system can be shaken to form a semi-stable emulsion or mixture which is stable for a time sufficient for spraying.

Another approach to significantly reducing or totally eliminating VOC in hair fixatives is the use of water-dispersable or water-soluble polymers in an aqueous-based hair fixative gel. Such gels which are available currently utilize poly(vinyl pyrrolidone) (PVP) or derivatives thereof, such as poly(vinyl pyrrolidone/vinyl acetate) copolymers (PVPNA), as the hair fixative resin contained therein. PVP has relatively low glass transition temperature, i.e., about 80° C., and is very sensitive to water or humidity. It is desirable, then, to find a water-soluble polymer to replace PVP. The polymer should be less sensitive to water, form clear films upon drying, and provide the hair fixative gels with hair fixative properties which are as good as or better than hair fixative gels which contain PVP as the fixative resin.

SUMMARY OF THE INVENTION

The present invention relates to hair fixative compositions which utilize as the hair fixative resin a polymer which is prepared from N-vinyl formamide (NVF). The polymer may be a homopolymer of NVF or an interpolymer of NVF and at least one vinyl monomer(s). The polymer is present in amounts effective to provide the inventive hair fixative compositions with hair fixative properties. In preferred embodiments, the hair fixative composition is a stable, aqueous gel which forms a clear, non-tacky film upon drying. In certain embodiments, the gel has a rheology effective to allow the gel to be applied to the hair via a spray pump.

DETAILED DESCRIPTION OF THE INVENTION

N-vinyl formamide (NVF) polymerizes to form a non-ionic, water-soluble polymer which has a Tg of about 147° C. and which forms clear, non-tacky films upon drying. The present invention is directed to hair fixative compositions which utilize as the hair fixative resin therein water-soluble polymers which are prepared from N-vinyl formamide. N-vinyl formamide monomer is available from Air Products and Chemicals, Inc., Allentown, PA., under the trade name Vinamer™ EF. Processes for preparing N-vinyl formamide are disclosed in U.S. Pat. Nos. 4,578,515, 4,906,777, 4,942, 259 and 5,037,927, all of which are hereby incorporated by reference in their entirety.

An indication of the relative water solubility of NVF versus PVP may be noted in the respective copolymers of vinyl acetate (VA). PVP/VA copolymers may contain up to 40 weight percent of VA and still yield clear solutions of the copolymer in water. On the other hand, NVF/VA copolymers containing greater than about 5 weight percent of VA do not yield such clear solutions, indicating that PVP is more soluble in water than NVF.

In order to function as a hair fixative, the composition and the hair fixative resin must possess certain hair fixative properties. For instance, the compositions must be capable of forming flexible, clear, low-tack or non-tacky films at room temperature. Once applied to the hair, the films must possess sufficient stiffness and humidity resistance to hold the hair in place under conditions normally encountered by the user thereof, yet must be readily removable from the hair by conventional shampoos and/or water. The polymer will preferably have a glass transition temperature (Tg) which is effective to form clear, low tack or non-tacky films at room temperature. If the Tg is too low, the films formed may be too tacky and may not possess adequate stiffness and humidity resistance.

The polymer may be a homopolymer of N-vinyl formamide or may be an interpolymer prepared from N-vinyl formamide and at least one vinyl monomer(s). Preferably, the interpolymer will comprise at least about 20 weight percent of NVF, with the balance of the vinyl monomer(s). The term "vinyl monomer", as used herein, refers to vinyl monomers which are copolymerizable with the N-vinyl formamide. Suitable vinyl monomers include, (a) styrene and derivatives thereof, (b) $C_1$–$C_{18}$ alkyl esters of acrylic acid, (c) $C_1$–$C_{18}$ alkyl esters of methacrylic acid, (d) vinyl esters of the formula $CH_2=CH\text{-}OCOR$ where R is $C_1$–$C_{18}$, (e) alkyl substituted acrylamides and methacrylamides of the formula $CH_2=CR\text{-}CONR_1R_2$ where R is H or $CH_3$; $R_1$ is H or $C_1$–$C_{12}$ and $R_2$ is $C_1$–$C_{18}$, (f) monoesters and diesters of fumaric, itaconic and maleic acids, (g) vinyl ethers such as methyl vinyl ether, isobutyl vinyl ether and the like, (h) hydroxy functional acrylates and methacrylates such as hydroxyethyl acrylate, hydroxypropyl acrylate, hydroxyethyl methacrylate, hydroxypropyl methacrylate and the like, (i) amine monomers such as F-butylaminoethyl methacrylate, dimethylaminoethyl methacrylate, diethylaminoethyl methacrylate and the quarternized derivatives thereof such as trimethylmethacrylatoethyl ammonium chloride and trimethylmethacrylatoethyl ammonium sulfate, (j) acrylamide and non-alkyl substituted acrylamides such as diacetone acrylamide, and (k) cyclic amides such as vinyl pyrrolidone. Preferably, the vinyl comonomer is selected from the group consisting of methyl acrylate, methyl methacrylate, 2-hydroxyethyl acrylate, 2-hydroxyethyl methacrylate, 2-hydroxypropoyl acrylate, 2-hydroxypropyl methacrylate, vinyl acetate and oligoethylene glycol monomethacrylate.

The gel fixatives comprise as a hair fixative resin a homopolymer which is prepared from N-vinyl formamide, or interpolymers prepared from N-vinyl formamide and at least one vinyl monomer(s). The gel fixatives preferably are substantially free of organic hydrocarbon solvents and natural or synthetic oils, such as glycerol esters of higher even-numbered fatty acids, glycerides of palmitic stearic and oleic acid, liquid fatty acid esters, liquid fatty alcohols, paraffin oils, esters of polyhydric alcohols and polyethylene alcohols.

The hair fixative gels of the invention comprise an amount of the hair fixative polymer which is effective to impart hair fixative properties to the gels. Where the level of polymer is too high, the gels and films formed therefrom exhibit unacceptable haziness. Where the level of polymer is too low, properties such as stiffness and humidity resistance are adversely affected. Typically, the gels comprise from about 0.5 to about 15 weight percent of the polymer, preferably from about 1 to about 10 weight percent, and more preferably from about 2 to about 7 weight percent of the polymer, based on the total weight of the gel. The hair fixative gels also may comprise a gelling agent in amounts effective to form a gel. Preferably, the gels comprise from about 0.05 to about 1 weight percent of the gelling agent, more preferably from about 0.1 to about 0.6 weight percent of the gelling agent, based on the total weight of the hair fixative gel. Examples of such gelling agents include synthetic polymers such as the acrylic-based Carbopol® series of thickeners available from B. F. Goodrich, Cleveland, Ohio and associative thickeners such as Aculyn™, available from Rohm & Haas, Philadelphia, Pa. Other exemplary gelling agents include, cellulosic thickeners, such as derivatized hydroxyethyl cellulose and methyl cellulose, starch-based thickeners, such as acetylated starch, and naturally occurring gums, such as agar, algin, gum arabic, guar gum and xanthan gum.

In certain embodiments, the rheology will be such that the gels may be applied via a spray pump. That is to say, the gels will be shear thinning to the extent that they may be applied via a spray pump and retain their hair fixative properties once applied to the hair. As one skilled in the art will appreciate, the particular rheological properties required for a spray pump application may be dependent upon factors such as the spray nozzle utilized, gel composition, the solvent system utilized, if any, and the like. One skilled in the art, having the benefit of the teachings of the present invention, will be able to ascertain the particular rheological properties required for a particular spray pump application.

In other embodiments, the hair fixative compositions may be in the form of an aerosol or non-aerosol spray, a mousse or a hair-setting lotion. The compositions may be aqueous or non-aqueous, although aqueous hair fixative compositions are preferred. The compositions may contain propellants such as ethers, compressed gases, halogenated hydrocarbons and hydrocarbons. Exemplary propellants are dimethyl ether, propane, butane and 1,1-difluoroethane. Non-aqueous hair fixative compositions may further include solvents such as ethanol, isopropanol, acetone, dimethoxymethane and methyl ethyl ketone. The compositions may further include other materials or additives such as fragrances, preservatives, colorants, plasticizers, emulsifiers, conditioners, neutralizers, glossifiers and the like. Such propellants, solvents and materials or additives are commonly used in hair fixative compositions known heretofore.

The following examples are indicative of preferred hair fixative compositions and hair fixative polymers utilized therein. They are not intended and should not be construed to limit the scope of the claims appended hereto. All percentages noted herein are weight percent unless noted otherwise. With the exception of Polymer L, inherent viscosities (I.V.) were determined on 1 weight percent polymer in 1 N KCL aqueous solutions. The I.V. of Polymer L was determined on 1 weight percent polymer in water.

EXAMPLES

Preparation of NVF Homopolymers by Solution Polymerization

Into a 2-liter flask equipped with a stirring shaft powered by a mechanical stirrer, a water bath, a thermometer and a reflux condenser were added as an initial charge 22.5 grams of NVF, 53.5 grams of a 70:30 ethanol/water mixture (wt %), 25.0 grams of water and 1.12 grams of t-butyl peroctoate. The mixture was brought to reflux to allow formation of a solvent atmosphere blanket above the reagents. After 15 minutes of reflux, a monomer slow-add of a mixture of 177.5 grams NVF and 270 grams of water was continuously and regularly added over a 4 hour period. Two hours after the beginning of the monomer slow-add, a mixture of 26.5 grams of a 70:30 ethanol/water (wt %) and 0.2 gram of t-butyl peroctoate was added regularly and continuously over a 2 hour period. When the above slow-adds had been introduced, a post-scavenging slow-add composed of 37 grams of a 70:30 ethanol/water mixture (wt %) and 0.66 gram of t-butyl peroctoate was added regularly and continuously over a 3 hour period. This was followed by a 5 hour hold period during which reflux was also maintained. After cooling, the apparatus was modified to include a Dean-Stark trap. The organic solvent was distilled off, steam being introduced above the reaction mixture when the vapor temperature reached about 90° C. When the reflux temperature had reached 100° C., steam was injected subsurface and the operation maintained for 15 minutes. The aqueous solution appeared clear and was diluted to 20% solids content. The polymer had an I.V. of 1.61 and was designated Polymer A.

A second NVF homopolymer was prepared according the above procedure, except that 0.6 gram of beta-mercaptoethanol was included in the first monomer slow-add. The final aqueous solution appeared clear and was diluted to 20.4% solids. The polymer had an I.V. of 0.68 and was designated Polymer B.

Preparation of NVF Homopolymer by Precipitation Polymerization

The same apparatus was used as was described in Example. Into the flask was introduced an initial charge comprising 22.5 grams of NVF, 279 grams of ethyl acetate, and 1.12 grams of t-buty peroctoate. The mixture was brought to reflux to allow formation of a solvent atmosphere blanket above the reagents. After 15 minutes of reflux, a monomer slow-add comprising 177.5 grams of NVF and 330 grams of ethyl acetate was added regularly and continuously over a 4 hour period, refluxing conditions being maintained. Two hours after initiation of the above slow-add, a mixture of 26.5 grams of ethyl acetate and 0.2 gram of t-butyl peroctoate was added regularly and continuously over a 2 hour period. When the above slow-adds were completed, a post scavenging slow-add composed of 37 grams of ethyl acetate and 0.66 grams of t-butyl peroctoate was added regularly and continuously over a 3 hour period, refluxing conditions being maintained. The reactants were allowed to reflux for 5 hours. After cooling, the suspension was vacuum filtered and washed with ethyl acetate. The resulting white particles were dried overnight at 60° C. The polymer had an I.V. of 3.88 and was designated Polymer C.

Preparation of NVF/(meth)acrylate(s) Copolymer by Solution Polymerization

The following recipe is given for 200 grams of a copolymer of composition X% NVF and Y% (meth)acrylate.

Into a 2 liter flask equipped with a stirring shaft powered by a mechanical stirrer, a water bath, a thermometer and a reflux condenser were introduced as the initial charge 22.5 grams of monomers, so that the percent of (meth)acrylate monomer is Y×2/3; 53.5 grams of a 70:30 ethanol/water mixture (wt %), 10 grams of water and 1.12 grams of t-butyl peroctoate. The mixture was brought to reflux to allow formation of a solvent atmosphere blanket above the reagents. After 15 minutes of reflux, a monomer slow-add of a mixture of 113.2 grams of monomers so that the percent of (meth)acrylate monomer is Y and 190 grams of water were regularly and continuously added over a 3 hour period. Two hours after the beginning of the monomer slow-add, a mixture of 26.5 grams of a 70:30 ethanol/water (wt %) and 0.2 gram of t-butyl peroctoate was added regularly and continuously over a 2 hour period. When the first monomer slow-add was completed, it was immediately followed by a second monomer slow-add containing the remaining 64.3 grams of monomers and 60 grams of water, which was added regularly and continuously over a one hour period. When the above slow-adds had been introduced, a post-scavaging slow-add composed of 37 grams of a 70:30 ethanol/water mixture (wt %) and 0.66 gram of t-butyl peroctoate was added regularly and continuously over a 3 hour period. This was followed by a 5 hour hold period during which reflux was also maintained. After cooling, the apparatus was modified to include a Dean-Stark trap. The organic solvent was distilled off, steam being introduced above the reaction mixture when the vapor temperature reached about 90° C. When the reflux temperature had reached 100° C, steam was injected subsurface and the operation maintained for 15 minutes.

The following copolymers were prepared using the above procedure:

Polymer D: 90 NVF/10 HPA. The final aqueous solution appeared translucent and had an I.V. of 1.80.

Polymer E: 95 NVF/5 MA. The final aqueous solution appeared clear and had an I.V. of 1.40.

Polymer F: 90 NVF/10 HEA. The final aqueous solution appeared slightly translucent and had an I.V. of 1.44.

Polymer G: 90 NVF/10 HEMA. The final aqueous solution appeared translucent and had an I.V. of 1.25.

Polymer H: 95 NVF/5 HEM-5. The final aqueous solution appeared clear and had an I.V. of 1.74.

Polymer I: 95 NVF/5 MMA. The final aqueous solution appeared translucent and had an I.V. of 2.35.

Polymer J: 90 NVF/10 HPMA. The final aqueous solution appeared opaque and had an I.V. of 2.48.

Polymer K: 85 NVF/15 HPA. The final aqueous solution appeared translucent and had an I.V. of 1.38.

HEA=2-hydroxyethyl acrylate

HPA=2-hydroxypropyl acrylate

MA=methyl acrylate

HEMA=2-hydroxyethyl methacrylate

HPMA=2-hydroxypropyl methacrylate

MMA=methyl methacrylate

HEM-5=oligoethylene glycol monomethacrylate (obtained from Rhone-Poulenc under the trade name Sipomer HEM-5)

Preparation of NVF/Vinyl acetate (VA) copolymers by Solution Polymerization

Into a 2-liter flask equipped with a stirring shaft powered by a mechanical stirrer, a water bath, a thermometer and a reflux condenser were added as an initial charge 12.5 grams of NVF, 10 grams of vinyl acetate, 63.5 grams of a 70:30 ethanol/water mixture (wt %), 10 grams of water and 1.12 grams of t-butyl peroctoate. The mixture was brought to reflux to allow formation of a solvent atmosphere blanket above the reagents. After 15 minutes of reflux, a monomer slow-add of a mixture of 177.75 grams NVF and 250 grams of water were added regularly and continuously over a 4 hour period. Two hours after the beginning of the monomer slow-add, a mixture of 26.5 grams of a 70:30 ethanol/water (wt %) and 0.2 gram of t-butyl peroctoate was added regularly and continuously over a 2 hour period. When the above slow-adds had been introduced, a post-scavaging slow-add composed of 37 grams of a 70:30 ethanol/water mixture (wt %) and 0.66 gram of t-butyl peroctoate was added regularly and continuously over a 3 hour period. This was followed by a 5 hour hold period during which reflux was also maintained. After cooling, the apparatus was modified to include a Dean-Stark trap. The organic solvent was distilled off, steam being introduced above the reaction mixture when the vapor temperature reached about 90° C. When the reflux temperature had reached 100° C, steam was injected subsurface and the operation maintained for 15 minutes. The final aqueous solution appeared clear, had an I.V. of 0.95 and was designated Polymer L.

The following NVF/vinyl acetate copolymers were prepared according to the above procedure, adjusting the monomers according to the relative percentages.

Polymer M: 78 NVF/22 VA. The final aqueous solution appeared very yellow and opaque.

Polymer N: 50 NVF/50 VA. The final aqueous solution appeared opaque and yellowish.

Polymer 0:50 NVF/50 VA. The final copolymer appeared to be a white fluid.

Preparation of Gel Compositions

Polymers A through O were formulated into hair fixative gel compositions according to the following formulation. All values reported are parts by weight, based on the total weight of the gel composition.

|  | Ingredient | Parts by Weight |
|---|---|---|
| Part A | NVF polymer | 3.00 |
|  | triethanolamine (TEA) | 0.60 |
|  | deionized water | 47.85 |
| Part B | Carbopol ® 940 | 0.6 |
|  | Dowicil ® 200 (preservative) | 0.10 |
|  | deionized water | 47.85 |
|  |  | 100 |

The polymer and TEA were mixed in D.I. water until homogenous. In a separate vessel, the Dowicil® 200 preservative and Carbopol® 940 thickener were combined with D.I. water and mixed until the Carbopol® went into solution. Dowicil® 200 is available from The Dow Chemical Company, Midland, Mich. Parts A and B were then combined and mixed gently until a clear viscous gel was formed.

High Humidity Curl Retention Test Protocol

Each of the gels was tested on nine dampened 10-inch swatches of European Brown hair. To each swatch was applied 0.5 g of the respective gel composition. The gel was worked into the swatch, which then was curled end-over-end on a 0.5 inch teflon mandrel. The curl was then carefully removed from the mandrel and secured with two hair clips. The curl was then placed in an oven at a temperature of 120° F. overnight. The dried curl was gently unwound and hung on a graduated, transparent curl retention board contained in a humidity chamber at 90% relative humidity and 70° F. Percent curl retention was measured at 15, 30, 60, 90 and 120 minutes. Curl retention is calculated as below. The mean % retention obtained at each time interval are compared, statistically analyzed and reported at the 95% confidence level.

$$\text{Curl Rentention} = \frac{L - L_f}{L - L_o} \times 100$$

L=Length of swatch fully extended
$L_o$=Length of curl before exposure
$L_f$=Length of curl after exposure Stiffness Test Protocol Each of the gels was tested on three dampened 4.5 inch Brown Virgin Italian hair swatches. To each swatch was applied 0.25 g of the respective gel. The gel was worked into the swatch and each swatch dried in an oven at 110° F. for two hours. The swatches were placed in a constant temperature and humidity chamber at 50% relative humidity and 23° C. and allowed to remain therein overnight. The stiffness of the swatches were measured using appropriate device for measuring stiffness. The results were statistically analyzed and reported at the 95% confidence level.

EXAMPLE 1

Gels formulated with Polymers A, B, D, E, F and G were compared for high humidity curl retention and stiffness to PVP K-90 gels which were formulated with the Carbopol® 940 thickener. PVP K-90 is a homopolymer of vinyl pyrrolidone available from International Specialty Products, Wayne, N.J. Results are reported in Table 1.

TABLE 1

| | % HIGH HUMIDITY CURL RETENTION | | | | | |
|---|---|---|---|---|---|---|
| | 15 MIN. | 30 MIN. | 60 MIN. | 90 MIN. | 2 HR. | STIFF-NESS |
| POLYMER A | 94.85 | 82.34 | 74.60 | 59.15 | 56.24 | 364 |
| POLYMER B | 88.89 | 78.18 | 60.23 | 47.89 | 44.11 | 401 |
| POLYMER D | 91.36 | 82.06 | 71.12 | 60.64 | 57.98 | 416 |
| POLYMER E | 95.22 | 90.74 | 79.18 | 68.55 | 62.84 | 382 |
| POLYMER F | 89.48 | 83.37 | 73.65 | 64.70 | 59.92 | 388 |
| POLYMER G | 93.07 | 86.78 | 78.86 | 66.13 | 62.75 | 360 |
| PVP K-90 | 89.76 | 82.23 | 76.23 | 67.39 | 63.31 | 345 |

As the high humidity curl retention results indicate, there is no statistically significant differences between gels formulated with Polymers A, D, E, F, and G and the PVP K-90 comparative example gel. The gel formulated with Polymer B appeared to be inferior to the PVP K-90 gel.

With respect to stiffness, gels formulated with Polymers B, D and F were statistically superior to the PVP K-90 gel, with the remaining gels showing no statistically significant differences.

Gels formulated with Polymers A through F exhibited improved clarity over the PVP K-90 gel, while the gel formulated with Polymer G was less clear than the PVP K-90 gel.

EXAMPLE 2

Gels formulated with Polymers M, N and O were compared to the PVP K-90 gels as above. Results are reported in Table 2.

TABLE 2

| | % HIGH HUMIDITY CURL RETENTION | | | | | |
|---|---|---|---|---|---|---|
| | 15 MIN. | 30 MIN. | 60 MIN. | 90 MIN. | 2 HR. | STIFF-NESS |
| POLYMER M | 84.94 | 73.54 | 53.98 | 49.30 | 47.32 | 355 |
| POLYMER N | 83.55 | 69.16 | 51.27 | 45.72 | 42.56 | 295 |
| POLYMER O | 84.76 | 70.57 | 57.67 | 52.47 | 49.65 | 307 |
| PVP K-90 | 85.20 | 69.14 | 54.78 | 49.77 | 44.81 | 356 |

There are no statistically significant differences noted between gels formulated with Polymers M, N and O and the PVP K-90 comparative example.

Gels formulated with Polymers M exhibited comparable clarity to the PVP K-90 gel, while gels formulated with Polymers N and O were less clear than the PVP K-90 gel.

EXAMPLE 3

Gels formulated with Polymers C, H, I, J and L were compared to PVP K-90 as above. Results are reported in Table 3.

TABLE 3

|  | % HIGH HUMIDITY CURL RETENTION | | | | | |
| --- | --- | --- | --- | --- | --- | --- |
|  | 15 MIN. | 30 MIN. | 60 MIN. | 90 MIN. | 2 HR. | STIFF-NESS |
| POLYMER C | 89.93 | 82.28 | 71.92 | 66.10 | 64.72 | 300 |
| POLYMER H | 90.14 | 84.23 | 73.00 | 67.19 | 64.71 | 282 |
| POLYMER I | 87.73 | 79.12 | 68.46 | 61.71 | 60.21 | 249 |
| POLYMER J | 89.35 | 82.16 | 75.25 | 70.46 | 68.79 | 315 |
| POLYMER L | 86.54 | 79.95 | 72.31 | 66.08 | 65.44 | 414 |
| PVP K-90 | 87.48 | 80.82 | 71.35 | 65.61 | 63.84 | 270 |

There were no statistically significant differences between any of the inventive gels and the comparative PVP K-90 gel with respect to high humidity curl retention.

The gel formulated with Polymer L was statistically superior to the PVP K-90 gel, while there were no statistically significant differences between the PVP K-90 gels and gels prepared with Polymers C, H, I and J with respect to stiffness.

Gels formulated with Polymers C and H exhibited improved clarity over the PVP K-90 gel. Gels formulated with Polymers I and J exhibited comparable clarity to the PVP K-90 gel, while gel the formulated with Polymer L was less clear than the PVP K-90 gel.

EXAMPLE 4

A gel formulated with Polymer K was compared to the PVP K-90 gels as above. Results are reported in Table 4.

TABLE 4

|  | % HIGH HUMIDITY CURL RETENTION | | | | | |
| --- | --- | --- | --- | --- | --- | --- |
|  | 15 MIN. | 30 MIN. | 60 MIN. | 90 MIN. | 2 HR. | STIFF-NESS |
| POLYMER K | 94.15 | 88.81 | 77.11 | 58.67 | 42.21 | 260 |
| PVP K-90 | 91.21 | 80.49 | 61.62 | 45.55 | 36.19 | 203 |

Both curl retention and stiffness of the gel formulated with Polymer K were statistically superior to the PVP K-90 control gel.

The gel formulated with Polymer K exhibited improved clarity over the PVP K-90 gel.

We claim:

1. A hair fixative composition comprising, from about 0.5 to about 15 weight percent of a polymer prepared from N-vinyl formamide, wherein the polymer is selected from the group consisting of a homopolymer of N-vinyl formamide and an interpolymer of N-vinyl formamide and at least one vinyl monomer(s), a gelling agent in an amount effective to form a hair fixative gel; and a solvent selected from the group consisting of water, organic solvents, or mixtures thereof, wherein the hair fixative composition exhibits high humidity curl retention.

2. The hair fixative gel of claim 1, wherein the hair fixative gel is free of propellants.

3. The gel of claim 2 wherein the polymer comprises from about 100 to 20 weight percent of the N-vinyl formamide and from about 0 to 80 weight percent of at least one vinyl monomer(s).

4. The gel of claim 3 wherein the vinyl monomer(s) is selected from the group consisting of (a) styrene and derivatives thereof, (b) $C_1$–$C_{18}$ alkyl esters of acrylic acid, (c) $C_1$–$C_{18}$ alkyl esters of methacrylic acid, (d) vinyl esters of the formula $CH_2$=CH-OCOR where R is $C_1$–$C_{18}$, (e) alkyl substituted acrylamides and methacrylamides of the formula $CH_2$=CR-CONR$_1$R$_2$ where R is H or $CH_3$; $R_1$ is H or $C_1$–$C_{12}$ and $R_2$ is $C_1$–$C_{18}$, (f) monoesters and diesters of fumaric, itaconic and maleic acids, (g) vinyl ethers, (h) hydroxy functional acrylates and methacrylates, (i) amine monomers and the quaternized derivatives thereof, (j) acrylamide and non-alkyl substituted acrylamides, and (k) cyclic amides.

5. The gel of claim 4 wherein the gelling agent is selected from the group consisting of synthetic polymers, cellulosic thickeners, starch-based thickeners and naturally occurring gums.

6. The gel of claim 5 comprising from about 0.5 to about 15 weight percent of the polymer and from about 0.05 to about 1.0 weight percent of the gelling agent.

7. The gel of claim 6 wherein the vinyl monomer is selected from the group consisting of methyl acrylate, methyl methacrylate, 2-hydroxyethyl acrylate, 2-hydroxyethyl methacrylate, 2-hydroxypropyl acrylate, 2-hydroxypropyl methacrylate, vinyl acetate and oligoethylene glycol monomethacrylate.

8. The gel of claim 6 wherein the polymer comprises from about 90 to about 95 weight percent of the N-vinyl formamide and from about 10 to about 5 weight percent of the vinyl monomer selected from the group consisting of methyl acrylate, methyl methacrylate, 2-hydroxyethyl acrylate, 2hydroxyethyl methacrylate, 2-hydroxypropyl acrylate, 2-hydroxypropyl methacrylate and oligoethylene glycol monomethacrylate.

9. The gel of claim 4 comprising from about 1 to 10 weight percent of the polymer and wherein the polymer and the gelling agent are present at ratios of between about 1:1 to about 100:1.

10. The gel of claim 2 wherein the gel has a rheology effective to allow the gel to be applied via a spray pump.

11. The gel of claim 2 comprising from about 0.5 to about 15 weight percent of the polymer and a gelling agent in amounts effective to allow the gel to be applied by a spray pump.

12. The hair fixative gel composition of claim 2 wherein the solvent consists essentially of water.

13. The hair fixative composition of claim 1 wherein the vinyl monomer is selected from the group consisting of methyl acrylate, methyl methacrylate, 2-hydroxyethyl acrylate, 2-hydroxyethyl methacrylate, 2-hydroxypropyl acrylate, 2-hydroxypropyl methacrylate, and oligoethylene glycol monomethacrylate.

14. A method of fixing hair, comprising applying to the hair a hair fixative composition comprising from about 0.5 to about 15 weight percent of a polymer prepared from N-vinyl formamide, wherein the polymer is selected from the group consisting of a homopolymer of N-vinyl formamide and an interpolymer of N-vinyl formamide and at least one vinyl monomer(s), a gelling agent in an amount effective to form a hair fixative gel; and a solvent selected from the group consisting of water, organic solvents, or mixtures thereof, wherein the hair fixative gel exhibits high humidity curl retention.

15. The method of claim 14, wherein the hair fixative gel is free of propellants.

16. The method of claim 15 wherein the polymer comprises from about 1 00 to 20 weight percent of the N-vinyl formamide and from about 0 to 80 weight percent of the vinyl monomer(s).

17. The method of claim 16 wherein the vinyl monomer(s) is selected from the group consisting of (a) styrene and derivatives thereof, (b) $C_1$–$C_{18}$ alkyl esters of acrylic acid, (c) $C_1$–$C_{18}$ alkyl esters of methacrylic acid, (d) vinyl esters of the formula $CH_2$=CH-OCOR where R is $C_1$–$C_{18}$, (e) alkyl substituted acrylamides and methacrylamides of the formula $CH_2$=CR-$CONR_1R_2$ where R is H or $CH_3$; $R_1$ is H or $C_1$–$C_{12}$ and $R_2$ is $C_1$–$C_{18}$, (f) monoesters and diesters of fumaric, itaconic and maleic acids, (g) vinyl ethers, (h) hydroxy functional acrylates and methacrylates, (i) amine monomers and the quarternized derivatives thereof, (j) acrylamide and non-alkyl substituted acrylamides, and (k) cyclic amides.

18. The method of claim 17 wherein the vinyl monomer is selected from the group consisting of methyl acrylate, methyl methacrylate, 2-hydroxyethyl acrylate, 2-hydroxyethyl methacrylate, 2-hydroxypropyl acrylate, 2-hydroxypropyl methacrylate, and oligoethylene glycol monomethacrylate.

19. The method of claim 15 wherein the solvent consists essentially of water.

* * * * *

UNITED STATES PATENT AND TRADEMARK OFFICE
CERTIFICATE OF CORRECTION

PATENT NO. : 5,478,553
DATED : Dec. 26, 1995
INVENTOR(S) : Rama S. Chandran, et al It is certified that error appears in the above-indentified patent and that said Letters Patent is hereby corrected as shown below:

Column 3, line 5, Fbutylaminoethyl should read -- *t*-butylaminoethyl --.

Column 3, line 6, diethylaminoet-hyl should read -- diethylaminoethyl --.

Column 5, line 1, delete "in".

Column 5, line 2, delete "Example" and insert -- above -- therefore.

Column 5, line 4, *t*-buty should read -- *t*-butyl --.

Column 6, line 23, NVFNinyl should read -- NVF/Vinyl --.

Column 6, line 41, post-scavaging should read -- post-scavanging --.

Column 6, line 65, O:50 should read -- O: 50 --.

Signed and Sealed this

Ninth Day of July, 1996

*Attest:*

BRUCE LEHMAN

*Attesting Officer*  *Commissioner of Patents and Trademarks*